US012433982B2

(12) United States Patent
Jansson

(10) Patent No.: US 12,433,982 B2
(45) Date of Patent: Oct. 7, 2025

(54) PERITONEAL DIALYSIS CYCLER HAVING DISINFECTION

(71) Applicants: BAXTER INTERNATIONAL INC., Deerfield, IL (US); BAXTER HEALTHCARE SA, Glattpark (CH)

(72) Inventor: Olof Jansson, Vellinge (SE)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 466 days.

(21) Appl. No.: 17/981,635

(22) Filed: Nov. 7, 2022

(65) Prior Publication Data

US 2023/0146216 A1 May 11, 2023

Related U.S. Application Data

(60) Provisional application No. 63/278,290, filed on Nov. 11, 2021.

(51) Int. Cl.
*A61M 1/28* (2006.01)
*A61M 1/16* (2006.01)

(52) U.S. Cl.
CPC .......... *A61M 1/282* (2014.02); *A61M 1/1635* (2014.02); *A61M 1/1639* (2014.02); (Continued)

(58) Field of Classification Search
CPC .............. A61M 1/1635; A61M 1/1639; A61M 1/1686; A61M 1/1688; A61M 1/282; A61M 1/285
See application file for complete search history.

(56) References Cited

U.S. PATENT DOCUMENTS 4,618,343 A 10/1986 Polaschegg
5,542,919 A 8/1996 Simon et al.
2002/0107474 A1 8/2002 Noack et al.

FOREIGN PATENT DOCUMENTS

CA 2704411 C * 9/2016 .......... A61M 1/1605
DE 19830928 C1 5/1999

(Continued)

OTHER PUBLICATIONS

International Preliminary Report on Patentability from International Patent Application No. PCT/US2022/079376, mailed May 2, 2024. 17 pages.

(Continued)

*Primary Examiner* — John Kim
(74) *Attorney, Agent, or Firm* — K&L Gates LLP

(57) ABSTRACT

A peritoneal dialysis ("PD") system includes a first volumetric balancing chamber including a first fixed volume chamber and a first diaphragm positioned and arranged to extend back and forth within the first fixed volume chamber, the first diaphragm separating a fresh PD fluid side from a used PD fluid side of the first volumetric balancing chamber; a second volumetric balancing chamber including a second fixed volume chamber and a second diaphragm positioned and arranged to extend back and forth within the second fixed volume chamber, the second diaphragm separating a fresh PD fluid side from a used PD fluid side of the second volumetric balancing chamber; and a PD fluid pump positioned and arranged to pump used PD fluid back and forth between the used PD fluid sides of the first and second volumetric balancing chamber.

13 Claims, 5 Drawing Sheets

(52) U.S. Cl.
CPC ........ *A61M 1/1686* (2013.01); *A61M 1/1688* (2014.02); *A61M 1/285* (2013.01)

(56) References Cited

FOREIGN PATENT DOCUMENTS

| | | | |
|---|---|---|---|
| EP | 3466460 | A1 | 4/2019 |
| WO | WO2018036859 | A1 | 3/2018 |
| WO | WO2018202321 | A1 | 11/2018 |
| WO | WO2022146706 | A1 | 7/2022 |

OTHER PUBLICATIONS

Extended European Search Report dated Jan. 23, 2025, European Patent Application No. EP 24208948.0.

* cited by examiner

PERITONEAL DIALYSIS CYCLER HAVING DISINFECTION

PRIORITY CLAIM AND CROSS-REFERENCE TO RELATED APPLICATIONS

This application claims priority to and benefit of U.S. Provisional Patent App. No. 63/278,290 filed Nov. 11, 2021, titled PERITONEAL DIALYSIS CYCLER HAVING DISINFECTION, the entire contents of which are incorporated by reference herein in their entirety and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Continuous renal replacement treatment ("CRRT") is a blood treatment like HD, HF and HDF, but instead occurs in an acute setting, e.g., hospital, where the patient may be experiencing kidney failure due to an external cause placing the patient in the hospital. Because the patient is likely in the hospital for a prolonged period, CRRT can be run more slowly than a typical chronic HD treatment. CRRT treatments typically use bags of dialysis fluid (HD) or replacement fluid (HF and HDF) and are accordingly like peritoneal dialysis discussed next in that aspect (although certain HHD systems also used bagged dialysis fluid). CRRT treatments are however blood treatments that may be performed using an HD tubing arrangement (typical in the US) or an HF or HDF tubing arrangement (typical in Europe).

Another type of kidney failure therapy as mentioned above is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, fluid control is very important because such control controls the flow of fresh and used dialysis fluid to and from the patient. One HD machine provided by the assignee of the present disclosure controls fluid flow provided by fresh and used PD fluid pumps. A flow sensor is provided for each PD fluid pump. By pulling somewhat more used dialysis fluid from the dialyzer than the fresh dialysis fluid delivered to the dialyzer, as measured by the flow sensors, a desired amount of patient ultrafiltration ("UF") is achieved. While the method of control works well, the flow sensors can be expensive.

In any of the above modalities using an automated machine, the automated machine operates typically with a disposable set, which is discarded after a single use. Depending on the complexity of the disposable set, the cost of using one set per day may become significant. Also, daily disposables require space for storage, which can become a nuisance for home owners and businesses. Further, the disposable sets can create a large amount of hard and soft plastic waste. Moreover, daily disposable replacement requires daily setup time and effort by the patient or caregiver at home or at a clinic.

For each of the above reasons, it is desirable to provide an automated dialysis machine (blood and PD) that simplifies fresh and used dialysis fluid flow control and reduces disposable waste.

SUMMARY

Known automated peritoneal dialysis ("PD") systems typically include a machine or cycler that accepts and actuates a pumping cassette having a hard part and a soft part that is deformable for performing pumping and valving operations. The hard part is attached to tubes that extend to various bags. The disposable cassette and associated tubes and bags can be cumbersome for a patient or caregiver to load for treatment. The overall amount of disposable items may also lead to multiple setup procedures, which can expose room for error. The disposable items are expensive and cumbersome to dispose of as discussed above.

The automated PD system and associated methodology of the present disclosure, on the other hand, convert much of the fluid carrying portions of the PD system into reusable components, which are disinfected after treatment. Fluid lines within the machine or cycler are reused. Disposable items remaining may include the patient and drain lines, the dialysis fluid containers or bags and the solution lines. When not connected to fluid containers or bags, or to an online dialysis fluid generation source, the reusable dialysis fluid lines may be connected to dedicated disinfection connectors or to themselves. In either embodiment, the reconnected dialysis fluid lines form a disinfection loop, which allows for disinfection after treatment. It is contemplated to use either water or leftover dialysis fluid as the disinfecting fluid and to heat same to a disinfection temperature, e.g., between 65° C. or 75° C. and 130° C. The flow components, lines and tubes that are disinfected may be metal, e.g., stainless steel, or plastic, e.g., polyvinylchloride ("PVC") or a non-PVC material, such as polyethylene ("PE"), polyurethane ("PU") or polycarbonate ("PC").

Inside a housing of the machine or cycler, reusable tubing lines run through one or more dialysis fluid line valve. In an embodiment, any of the valves of the PD machine may be an electrically actuated solenoid valve having a reusable valve body that occludes (e.g., when unpowered) or allows (e.g., when powered) PD fluid to flow through the body. First and second dialysis fluid inline heaters may also be provided and be electrically actuated in one embodiment. One of the inline heaters is used to heat treatment fluid and is, for example, a resistive heater having a reusable heater body that accepts PD fluid for heating. The inline heater in an embodiment is able to heat PD fluid from room temperature to body temperature, e.g., 37° C., at a flowrate of at least 300 milliliters ("ml")/minute. One or more temperature sensor may be located adjacent to the heater, e.g., downstream from the heater, to provide feedback for temperature control. Because the present PD machine separates a fresh PD fluid side from a used PD fluid side, especially for disinfection/sterilization after treatment, the second heater is provided to disinfect the used PD fluid side of the PD machine. The second heater may be of the first type and have the same capabilities as the first heater. The first treatment fluid heater is used additionally after treatment to sterilize the fresh PD fluid side of the PD machine.

The machine embodiments discussed herein include a single, reusable PD fluid pump, such as an accurate volumetric pump. The reusable pump includes a reusable pump body that accepts used PD fluid for pumping. That is, the pump does not require the dialysis fluid to flow within a disposable item, such as a tube or cassette. The reusable volumetric PD fluid pump may be an electrically operated piston, membrane or gear pump, which may be inherently accurate. The PD fluid pump is bidirectional and continuous in one embodiment. The PD fluid pump is in one embodiment placed in a used PD fluid pathway such that the pump pumps used PD fluid back and forth between two volumetric balancing chambers to force fresh PD fluid to a desired location during a patient fill. That is, the PD fluid pump using used PD fluid draws fresh PD fluid into the volumetric balancing chambers and discharges fresh PD fluid from the volumetric balancing chambers. The PD fluid pump also pumps used PD fluid from the patient to drain during a patient drain.

The volumetric balancing chambers each include a well-defined volume chamber separated by a membrane or diaphragm. The diaphragm is able to flex back and forth within the chamber to dispel a volume of fluid, e.g., fresh PD fluid by receiving the same volume of used fluid on the other side of the diaphragm. The volumetric balancing chambers allow a single PD fluid pump to be used. The single PD fluid pump pumps to each of the volumetric balancing chambers as determined by the states of the associated valves. The valves are sequenced to direct fresh or used PD fluid to or from the volumetric balancing chambers and to enable fresh or used dialysis fluid to be delivered from the chambers to the patient or to drain, respectively. The volumetric balancing chambers also perform a supervisory task in that their known volume outputs may be used to check that the stroke volume of the piston pump does not change over time.

Certain embodiments discussed herein also include one or more airtrap to trap air removed from the PD fluid and to provide a bolus or buffer of dialysis fluid. The airtrap may also be involved in the disinfection sequence at the end of treatment. The airtraps may be located for example in the fresh and used PD fluid lines. A vent valve may be provided off of the top of the airtrap, which vents air from the airtrap to atmosphere for example and may be used during the disinfection sequence. In an embodiment, one or more level sensor is located adjacent each airtrap so that a desired level or range of levels of fresh and used PD fluid may be maintained in the airtrap.

Each of the embodiments discussed herein may also include one or more pressure sensor for detecting the pressure of fresh and used PD fluid. The pressure sensors output positive and negative patient pumping pressure signals, which are used to ensure that patient pumping pressure limits are not exceeded. Since used PD fluid is employed to drive the fresh PD fluid, the one or more pressure sensor may be provided in the used PD fluid pathway, e.g., on the negative sides of the volumetric balancing chambers, and may also be monitored to control a resulting positive fresh PD fluid pumping pressure. One or more temperature compensated conductivity sensor may also be provided for the evaluation of used PD fluid if desired.

The PD machines or cyclers of the present disclosure include a control unit having one or more processor and one or more memory that receive signals or outputs from the pressure sensors, the one or more temperature sensor, and the conductivity sensor and process the signals or outputs as feedback. The control unit uses pressure feedback to control the PD fluid pump to pump at safe pressure limits during treatment and at safe system limits during disinfection. The control unit uses temperature feedback to control the dialysis fluid heater to heat the fresh dialysis fluid to, e.g., body temperature. The control unit also counts strokes executed by the volumetric balancing chambers to determine a total amount of fresh dialysis fluid delivered to the patient. The control unit monitors the PD fluid pump to determine the total amount of used dialysis fluid removed from the patient. The control unit also compares those amounts to determine an overall amount of ultrafiltration ("UF") removed from the patient.

The control unit also opens and closes the dialysis fluid valves to sequence the volumetric balancing chambers in combination with the operation of the PD fluid pump to run a priming sequence, a treatment sequence and a "germ deactivation" sequence after treatment. The control unit also powers the heater during the treatment and disinfection sequences.

The two sides (fresh versus used) of the volumetric balancing chambers are totally separated from each other, including in a disinfection mode of the present disclosure. The two different sides may therefore be "cleaned" after treatment using different approaches, e.g., sterilization of the fresh side and disinfection of the drain side. One important advantage of separating the flow paths as is done in the present disclosure is that the majority of "sensitive" flow path components (pump, pressure sensors, conductivity cell, etc.) may be positioned on the used PD fluid side, which sees the lowest temperature during "germ deactivation" (a term used herein to include either sterilization or disinfection or both). The result is a longer life duration or number of operations for the flow path components. The division also allows the fresh PD flow path to be greatly minimized, minimizing the amount of actual sterilization needed.

It is also contemplated that the disinfection temperature on the used PD fluid side of the flow path be maintained at a lower value than what is used in today's dialysis machines. One machine today uses a maximum temperature during a disinfection cycle of around 85° C. The heating sequence in the prior art machine is about thirty-seven minutes resulting an A0 disinfection value of about 1440 (requirement is to be over 900). With the APD cycler of the present disclosure, the disinfection time may be allowed to be extended, allowing that disinfection temperature to be lowered and still reach an A0 value of above 900. In an example, heating the used PD fluid flow path to 75° C., assuming a flow path volume of 100 to 150 ml, means that an A0 disinfection value of 900 may be reached within roughly forty-seven minutes. Should a shorter disinfection time be required, e.g., to be performed just before a treatment, an 85° C. or higher disinfection temperature could be used instead.

Sterilization of the fresh side of the volumetric balancing chambers in an embodiment needs to reach a sterilization grade temperature, e.g., a fluid temperature at or above 120° C., which is maintained for 15 to 20 minutes. With a small fresh PD fluid flow path volume, sterilization parameters are fully feasible. Note that the fresh and used PD fluid paths need to be "germs deactivated" in a sequence, they cannot completely overlap in one embodiment. The total time for a complete "germs deactivation" sequence may therefore be somewhere between an hour and one and a half hours.

In light of the disclosure set forth herein, and without limiting the disclosure in any way, in a first aspect of the present disclosure, which may be used with any other aspect, or portion thereof, a peritoneal dialysis ("PD") system includes a first volumetric balancing chamber including a first fixed volume chamber and a first diaphragm positioned and arranged to extend back and forth within the first fixed volume chamber, the first diaphragm separating a fresh PD fluid side from a used PD fluid side of the first volumetric balancing chamber; a second volumetric balancing chamber including a second fixed volume chamber and a second diaphragm positioned and arranged to extend back and forth within the second fixed volume chamber, the second diaphragm separating a fresh PD fluid side from a used PD fluid side of the second volumetric balancing chamber; and a PD fluid pump positioned and arranged to pump used PD fluid back and forth between the used PD fluid sides of the first and second volumetric balancing chambers.

In a second aspect of the present disclosure, which may be used with any other aspect, or portion thereof, the PD system includes at least one valve in fluid communication with the fresh PD fluid side of one of the first or second volumetric balancing chambers, and wherein fresh PD fluid is discharged from the fresh PD fluid side through the at least one valve when the PD fluid pump pumps used PD fluid to the used PD fluid side of the first or second volumetric balancing chamber.

In a third aspect of the present disclosure, which may be used with any other aspect, or portion thereof, the PD system includes a control unit configured to operate the PD fluid pump, the control unit configured to determine an amount of fresh PD fluid discharged from the fresh PD fluid side of the first or second volumetric balancing chamber via (i) monitoring a pumping output of the PD fluid pump and/or (ii) using a known volume of the first or second fixed volume chamber.

In a fourth aspect of the present disclosure, which may be used with any other aspect, or portion thereof, the PD system includes at least one valve in fluid communication with the fresh PD fluid side of the first or second volumetric balancing chamber, and wherein fresh PD fluid is drawn into the fresh PD fluid side through the at least one valve when the PD fluid pump pumps used PD fluid from the used PD fluid side of the first or second volumetric balancing chamber.

In a fifth aspect of the present disclosure, which may be used with any other aspect, or portion thereof, the PD system is configured during a patient drain such that the PD fluid pump pumps used PD fluid through a patient line, through one of the first or second volumetric balancing chambers, and through a drain line.

In a sixth aspect of the present disclosure, which may be used with any other aspect, or portion thereof, the PD fluid pump pumps used PD fluid through a return lumen of the patient line, and wherein the patient line further includes an output lumen for delivering fresh PD fluid to a patient.

In a seventh aspect of the present disclosure, which may be used with any other aspect, or portion thereof, the PD system includes a control unit configured to operate the PD fluid pump during the patient drain, the control unit configured to determine an amount of used PD fluid removed during the patient drain via monitoring at least one pumping output of the PD fluid pump.

In an eighth aspect of the present disclosure, which may be used with any other aspect, or portion thereof, the PD system includes a first heater in fluid communication with the fresh PD fluid sides of the first and second volumetric balancing chambers, and a second heater in fluid communication with the used PD fluid sides of the first and second volumetric balancing chambers, wherein the first heater is used in a sterilization sequence and the second heater is used in a disinfection sequence.

In a ninth aspect of the present disclosure, which may be used with any other aspect, or portion thereof, the first heater is further used to heat fresh PD fluid for treatment.

In a tenth aspect of the present disclosure, which may be used with any other aspect, or portion thereof, the first heater heats fresh PD fluid to at least 120° C. for the sterilization sequence, and the second heater heats fresh or used PD fluid to at least 65° C. for the disinfection sequence.

In an eleventh aspect of the present disclosure, which may be used with any other aspect, or portion thereof, the PD system includes a sterilization loop including the fresh PD fluid sides of the first and second volumetric balancing chambers and at least one of (i) at least one reusable solution line or (ii) at least one sealed cover that closes over at least one patient line port and/or drain line port.

In a twelfth aspect of the present disclosure, which may be used with any other aspect, or portion thereof, the PD system includes a disinfection loop including the used PD fluid sides of the first and second volumetric balancing chambers and at least one sealed cover that closes over at least one patient line port and/or drain line port.

In a thirteenth aspect of the present disclosure, which may be used with any other aspect, or portion thereof, the PD system is configured to run a patient drain in which (i) the first and second volumetric balancing chambers are bypassed and the accuracy of PD fluid pump is relied upon or (ii) the first and second volumetric balancing chambers are operated.

In a fourteenth aspect of the present disclosure, which may be used with any other aspect, or portion thereof, a peritoneal dialysis ("PD") system includes a first volumetric balancing chamber including a first fixed volume chamber and a first diaphragm positioned and arranged to extend back and forth within the first fixed volume chamber, the first diaphragm separating a fresh PD fluid side from a used PD fluid side of the first volumetric balancing chamber; a second volumetric balancing chamber including a second fixed volume chamber and a second diaphragm positioned and arranged to extend back and forth within the second fixed volume chamber, the second diaphragm separating a fresh PD fluid side from a used PD fluid side of the second volumetric balancing chamber; and a first heater in fluid communication with the fresh PD fluid sides of the first and second volumetric balancing chambers, and a second heater in fluid communication with the used PD fluid sides of the first and second volumetric balancing chambers, wherein the first heater is used in a sterilization sequence and the second heater is used in a disinfection sequence.

In a fifteenth aspect of the present disclosure, which may be used with any other aspect, or portion thereof, the PD system includes a sterilization loop including the fresh PD fluid sides of the first and second volumetric balancing chambers and at least one of (i) at least one reusable solution line or (ii) at least one sealed cover that closes over at least one patient line port and/or drain line port.

In a sixteenth aspect of the present disclosure, which may be used with any other aspect, or portion thereof, the PD system includes a disinfection loop including the used PD fluid sides of the first and second volumetric balancing chambers and at least one sealed cover that closes over at least one patient line port and/or drain line port.

In a seventeenth aspect of the present disclosure, which may be used with any other aspect, or portion thereof, a peritoneal dialysis ("PD") system includes a sterilization loop including a fresh PD fluid side of a PD machine; a disinfection loop including a used PD fluid side of the PD fluid machine; and a control unit configured to run a sterilization sequence in the sterilization loop and a disinfection sequence in the disinfection loop.

In an eighteenth aspect of the present disclosure, which may be used with any other aspect, or portion thereof, the sterilization loop includes a fresh PD fluid side of at least one volumetric balancing chamber, and wherein the disinfection loop includes a used PD fluid side of the at least one volumetric balancing chamber.

In a nineteenth aspect of the present disclosure, which may be used with any other aspect, or portion thereof, the disinfection loop includes at least one reusable solution line, and wherein the disinfection loop includes at least one sealed cover that closes over at least one patient line port and/or drain line port.

In a twentieth aspect of the present disclosure, which may be used with any other aspect, or portion thereof, any of the features, functionality and alternatives described in connection with any one or more of FIGS. 1 to 5 may be combined with any of the features, functionality and alternatives described in connection with any other of FIGS. 1 to 5.

In light of the above aspects and the present disclosure set forth herein, it is an advantage of the present disclosure to provide a PD fluid machine and associated system that reuses many components, which may otherwise be disposable.

It is another advantage of the present disclosure to provide fluid handling components that accept dialysis fluid directly without having to operate with a disposable item, such as a tube or flexible sheeting.

It is a further advantage of the present disclosure to provide the majority of the fluid handling components on a used PD fluid side of the PD fluid machine where the components only have to be subjected to a disinfection temperature (less than a sterilization temperature) after treatment.

It is yet another advantage of the present disclosure to provide a single volumetric pump that may be used to pump both fresh and used PD fluid.

It is still another advantage of the present disclosure to provide a PD machine and associated system, which requires only a small volume to be sterilized.

It is still another advantage of the present disclosure to provide a dialysis fluid machine and associated system that may use leftover treatment fluid during disinfection.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
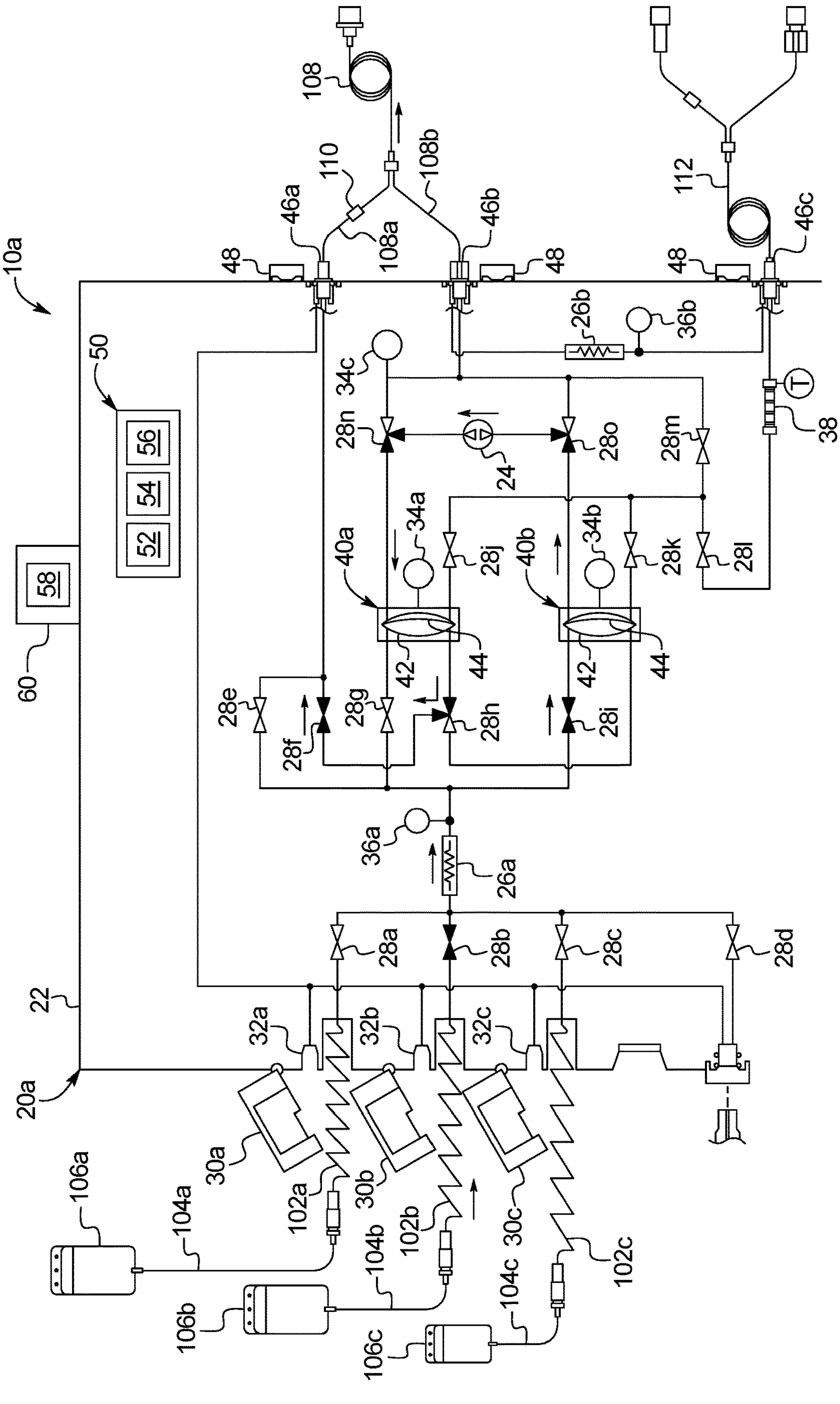
FIG. 1 is a schematic view of one embodiment of a peritoneal dialysis ("PD") machine and associated system having a single pump located on a used PD fluid side of the machine.

Referring now to the drawings and in particular to FIG. 1, a peritoneal dialysis ("PD") system 10*a* and associated methodology of the present disclosure includes a PD machine 20*a*. System 10*a* and PD machine 20*a* (as do other systems and machines or cyclers described herein) attempt to eliminate disposable items as much as possible and instead provide a majority of its fluid carrying portions as reusable components, which are disinfected after treatment. PD machine 20*a* includes a housing 22 that holds the reusable flow components and tubes or lines described herein. Any of the housing and reusable flow components and lines discussed herein may be made of metal, e.g., stainless steel, steel (for non-fluid contacting components) or aluminum (for non-fluid contacting components), or plastic, e.g., polyvinylchloride ("PVC") or a non-PVC material, such as polyethylene ("PE"), polyetereterketon ("PEEK"), polyurethane ("PU") or polycarbonate ("PC").

PD machine 20*a* includes a PD fluid pump 24, such as an electrically operated piston, membrane or gear pump, which may be inherently accurate. PD machine 20*a* in the illustrated embodiment includes two heaters 26*a* and 26*b*, such as an inline heaters. Heater 26*a*, which is the treatment fluid heater, is capable of heating PD fluid from room temperature or colder to body temperature, e.g., 37° C., at a flowrate of at least 300 milliliters ("ml")/minute (typical PD fill and drain flowrates are 200 to 300 ml/min). Heaters 26*a* and 26*b* are both used for "germ deactivation" (a term used herein include either sterilization or disinfection or both) at the end of treatment. Heater 26*a* is used for sterilization, while heater 26*b* is used for disinfection. Sterilization requires higher temperatures as discussed herein. Heaters 26*a* and 26*b* may both be capable of obtaining sterilization temperatures and may be the same or different heaters with the same or different capabilities.

PD machine 20*a* includes a plurality of valves 28*a* to 28*o*, which may be electrically actuated solenoid valves having a reusable valve body that occludes (e.g., when unpowered) or allows (e.g., when powered) dialysis fluid to flow through the body. Valves 28*a* to 28*d* are solution or supply valves. Valves 28*e* to 28*i* are fresh dialysis fluid inlet/outlet valves. Valves 28*j* to 28*m* are used dialysis fluid inlet/outlet valves. Valves 28*n* and 28*o* are toggling valves that allow used dialysis fluid to be pumped back and forth between volumetric balancing chambers 40*a* and 40*b*. Valves 28*n* and 28*o* may also be used when system 10*a* detects air in a pump chamber. Toggling valves 28*n* and 28*o*, like valve 28*h*, are three-way valves that switch flow path positions or orientations upon electrical actuation.

Although not illustrated in system 10*a* of FIG. 1, one or more airtrap may be provided, which operates with one or more level sensor located adjacent the airtrap, so that a desired level or range of levels of fresh or used PD fluid may be maintained in the airtrap. The level sensors may be ultrasonic, capacitance, inductive or optical sensors capable of discerning between fresh or used PD fluid versus air inside the airtrap.

PD machine 20*a* further includes temperature sensors 36*a* and 36*b* located adjacent to inline heaters 26*a* and 26*b*, respectively. In the illustrated embodiment, temperature sensors 36*a* and 36*b* are located downstream from heaters 26*a* and 26*b*. Third and fourth temperature sensors may also be located upstream from heaters 26*a* and 26*b*. The output from temperature sensors 36*a* and 36*b* are used as feedback to control how much power is supplied to inlet heaters 26*a* and 26*b* when fresh or used PD fluid is flowing through same.

Dialysis machine 20*a* also includes a plurality of pressure sensors 34*a* to 34*c*. The outputs from pressure sensors 34*a* to 34*c* are used to make sure that the pumping of fresh PD fluid to the patient is performed within a safe positive pressure limit, e.g., one to five psig (e.g., two psig (14 kPa), and that the pumping of used PD fluid from the patient is performed within a safe negative pressure limit, e.g., −1.0 psig to −3.0 psig (e.g., −1.3 psig (−9 kPa)). Pressure sensors 34*a* to 34*c* are each illustrated as being on the used PD fluid side of PD machine 20*a*, which is advantageous because they maximally see the disinfection temperature after treatment (as opposed to a higher sterilization temperature). The outputs from pressure sensors 34*a* and 34*b* associated with volumetric balancing chambers 40*a* and 40*b*, respectively, are nevertheless able to be used to control and monitor positive fresh PD fluid pumping pressures because the used PD fluid is used to drive the fresh PD fluid. The pressure of the used PD driving fluid is translated to and is thus the same as the driven fresh PD fluid.

PD machine 20*a* further includes at least one conductivity sensor 38, which may be temperature compensated. In FIG. 1, conductivity sensor 38 is shown located to sense used PD fluid, the output of which may be used to evaluate the effectiveness of the PD treatment and/or to look for disease, such as peritonitis. Conductivity sensor 38 may also be used, e.g., in a priming scenario, to measure the conductivity of fresh PD fluid to confirm that the fluid meets a prescribed PD fluid. Locating conductivity sensor 38 in the used PD fluid side of PD machine 20*a* is also advantageous in that the conductivity sensor only needs to see the disinfection temperature after treatment.

PD machine 20*a* of system 10*a* includes a control unit 50 having one or more processor 52, one or more memory 54 and a video controller 56, which controls a display device 58 associated with a user interface 60 of the machine. Control unit 50 controls each of PD fluid pump 24, inline heaters 26*a*, 26*b*, and valves 28*a* to 28*o* according to the flow sequences discussed herein. Control unit 50 also receives outputs from level sensors (discussed below), pressure sensors 34*a* to 34*c*, temperature sensors 36*a*, 36*b* and one or more conductivity sensor 38, and uses those outputs for feedback purposes discussed herein and also for any readout(s) desired at display device 58.

User interface 60 may include a touchscreen overlay operable with display device 58 and/or one or more electromechanical button, such as a membrane switch for inputting user commands. User interface 60 displays information to the user at display device 58 and may also include one or more speaker for outputting alarms, alerts and/or voice guidance commands. User interface 60 may be provided with PD machine 20*a* as illustrated in FIG. 1 and/or be a remote user interface operating with control unit 50. Control unit 50 may also include a transceiver (not illustrated) and a wired or wireless connection to a network, e.g., the internet, for sending treatment data to and receiving prescription instructions from a doctor's or clinician's server interfacing with a doctor's or clinician's computer.

Volumetric balancing chambers 40*a* and 40*b* are passive components in that they do not receive electrical inputs and are not under direct control by control unit 50. Volumetric balancing chambers 40*a* and 40*b* are instead operated via fluid pressure as directed by their associated valves. Volumetric balancing chambers 40*a* and 40*b* each include a fixed volume chamber 42, which may be made of any medically safe material discussed herein. Fixed volume chambers 42 include a flexible diaphragm or membrane 44, which flexes back and forth to receive a volume of used PD and dispel a like volume of fresh PD fluid. Flexible diaphragms or membranes 44 may be made of a durable and medically safe rubber, e.g., silicone, which does not permanently deform over multiple uses.

Figure 2:
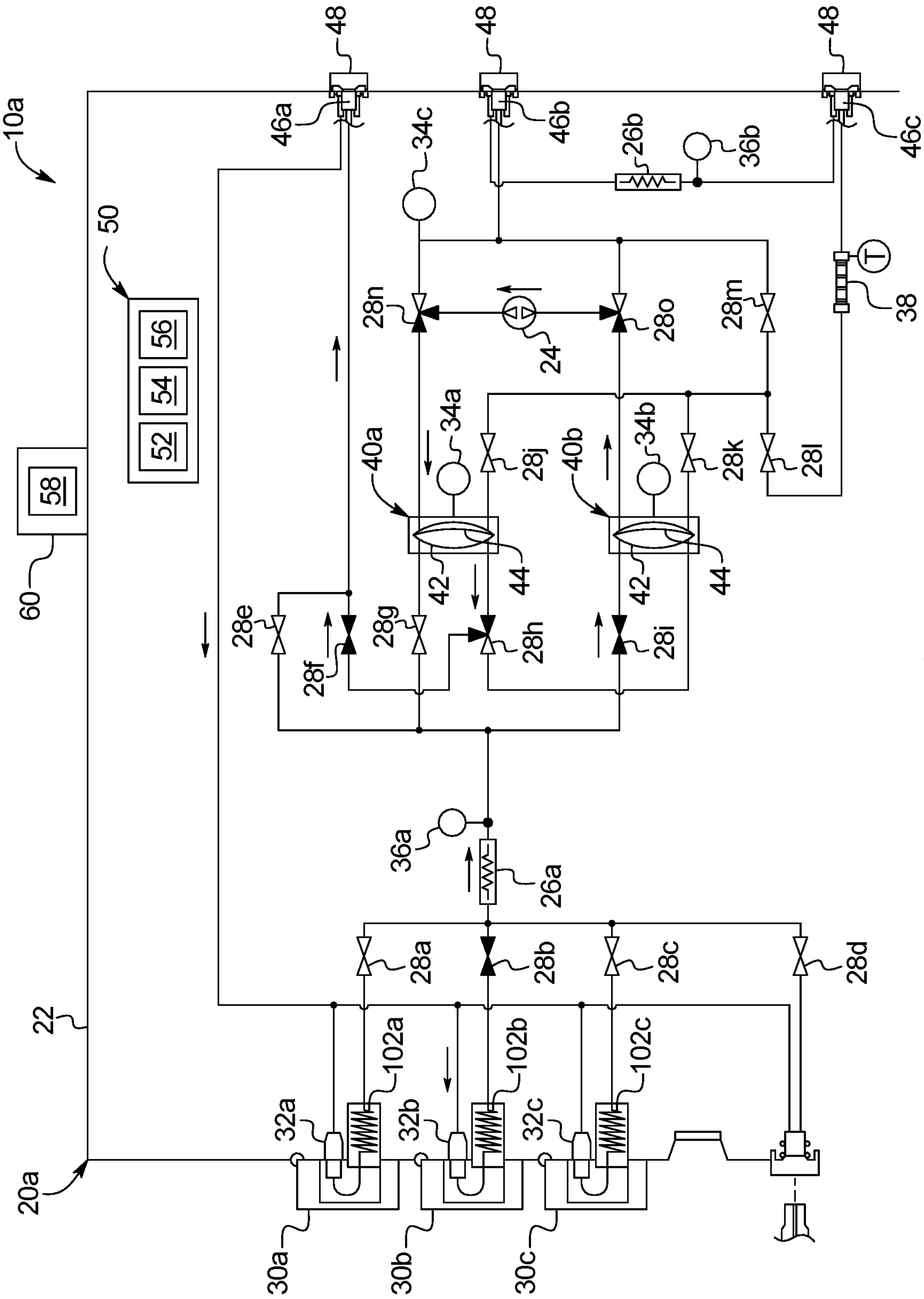
FIG. 2 is a schematic view of the embodiment of the PD machine and associated system of FIG. 1 in a sterilization/disinfection mode performing a "germ deactivation".

Housing 22 of PD machine 20*a* includes multiple features provided to aid the "germ deactivation" (sterilization and disinfection) performed after treatment. Housing 22 for example includes spring-loaded doors 30*a* to 30*c*, which cover reusable solution lines 102*a* to 102*c*, respectively, after treatment when reusable solution lines 102*a* to 102*c* are disconnected from disposable pigtails 104*a* to 104*c* extending from PD fluid containers 106*a* to 106*c*. As illustrated in FIG. 2, reusable solution lines 102*a* to 102*c* when disconnected are plugged into sterilization ports 32*a* to 32*c* provided in housing 22.

Housing 22 also includes an output port 46*a* that receives an output lumen 108*a* of a patient line 108. Housing 22 further includes a return port 46*b* that receives a return lumen 108*b* of patient line 108. Housing 22 additionally includes a drain port 46*c* that receives a drain line 112. Each of ports 46*a* to 46*c* is covered with a sealed cover 48, e.g., which spring-closes over ports 46*a* to 46*c*, when patient line 108 and drain line 112 are removed. Sealed covers 48 direct the sterilization fluid (port 46*a*) and the disinfection fluid (ports 46*b* and 46*c*) back into PD machine 20*a* and thereby help form the sterilization and disinfection loops, respectively.

In the illustrated embodiments herein, output lumen 108*a* is provided with a sterile, sterilizing grade filter 110, which provides a final level of sterilization to the fresh PD fluid prior to being delivered to the patient via patient line 108. Pore sizes for sterile, sterilizing grade filter 110 may, for example, be 0.1 to 0.2 micron. Suitable sterile, sterilizing grade filters may, for example, be Pall IV-5 or GVS Speedflow filters. It is envisioned that sterilizing grade filter 110 is eventually not needed or provided assuming that the fresh PD fluid side of system 10*a* has been sterilized properly. It is contemplated to perhaps provide sterilizing grade filter 110 until it is proven that proper sterilization is achievable and that the filter is not needed.

In FIGS. 1 to 5, valves that are darkened are open, while valves that are unshaded are closed. FIG. 1 illustrates a first PD machine 20*a*, which operates as part of system 10*a*, which also includes all disposable items, such as PD fluid containers 106*a* to 106*c* and their pigtails 104*a* to 104*c*, patient line 108 (including sterile, sterilizing grade filter 110 if provided) and drain line 112. In the systems of any of FIGS. 1 to 5, the patient may begin the treatment full of effluent from a previous treatment or be empty. Control unit 50 of PD machine 20*a* (and any of the PD machines discussed herein) may be programmed to start treatment by applying negative pressure to the patient. If the patient does not have effluent PD fluid to give, the patient is likely empty although patient line 108 could instead be kinked, which may be discovered or fixed by alarming or trying to clear the occlusion, respectively. Machine 20*a* may also be configured to check if the patient's fluid status is different than expected, e.g., perhaps the patient skipped a prescribed day fill. Control unit 50 may also be configured to initially try to push a small amount of PD fluid towards the patient to determine if a kink or other line occlusion exists. If a kink does not exist, then control unit 50 continues to the next programmed action. If a kink does exist, control unit 50 causes user interface 60 to issue an alarm.

If the patient is full of effluent at the beginning of treatment, PD machine 20*a* (and any of the PD machines discussed herein) senses same by causing PD fluid pump 24 to attempt to pull effluent from the patient through patient line 108 and return lumen 108*b*. Not sensing a resistance to the negative pressure, control unit 50 determines that the patient is full of effluent and continues with the initial drain. Control unit 50 here causes PD fluid pump 24 to continue pulling effluent from the patient through patient line 108 and return lumen 108*b*, through three-way valve 28*n* (for example), and for PD fluid pump 24 to push the effluent through three-way valve 28*o*, the effluent or used PD fluid side of volumetric balancing chamber 40*b*, and through valves 28*k* and 28*l*, drain port 46*c*, drain line 112 to a drain container or house drain (e.g., toilet or bathtub). In the above patient draining embodiment, PD fluid pump 24 needs to be an accurate pump, such as a piston pump, since volumetric balancing chambers 40*a* and 40*b* are bypassed.

In an embodiment, the accuracy of PD fluid pump 24 is relied on to know how much effluent has been removed during the patient drains (initial and subsequent drains). PD fluid pump 24 may for example be a piston pump that pumps a precise amount of effluent per every piston stroke. Control unit 50 accumulates the number of piston strokes over the course of multiple patient drains. A patient drain may end upon at least a minimum prescribed amount of effluent being removed from the patient. A patient drain may end alternatively upon control unit 50 receiving a characteristic pressure signal indicating that the patient is empty or virtually empty. The pressure signal to the control unit 50 may be from any one or more of pressure sensors 34*a* to 34*c*.

An alternative draining flow path through at least one volumetric balancing chamber may be used instead. In one example, used PD fluid is pumped into volumetric balancing chamber 40*b*. Control unit causes valves 28*i*, 28*g*, 28*j* and 28*l* to be open, while valve 28*k* is closed. Used PD fluid may also be drained from volumetric balancing chamber 40*a* to drain line 112. In the next half-cycle, volumetric balancing chamber 40*b* is initially full of patient effluent, while volumetric balancing chamber 40*a* is initially empty. Here, control unit 50 causes PD fluid to pump drained effluent towards volumetric balancing chamber 40*a*, which in turn pushes fresh fluid over to volumetric balancing chamber 40*b*, causing drained effluent to be pushed to drain line 112 via the now open valve 28*k* (valve 28*j* is here closed). In this alternative patient draining embodiment, PD fluid pump 24 may be a less accurate pump because volumetric balancing chambers 40*a* and 40*b* are used and provide volumetric accuracy. It is worth noting however that using a single accurate pump, such as a piston pump, is also advantageous because whatever error is present tends to cancel out when determining a patient's ultrafiltration ("UF") volume, which is a difference between one or more drain volume and one or more fill volume. If a presumption that the accurate pump tends to error in the same manner for a patient drain as a patient fill is correct, then the two errors, albeit small due to the accuracy of the pump, will cancel and yield an even more accurate UF removed volume. And it is more important for a PD treatment that UF volume is determined accurately. Volumetric balancing chambers 40*a* and 40*b* may be used as a supervisory or primary way of determining volume pumped, with the accurate pump volume used as a check.

If the patient is instead empty at the beginning of treatment, then control unit 50 transitions to an initial fill. Because there is no fluid on the used PD or effluent sides of volumetric balancing chambers 40*a* and 40*b* at this time, control unit 50 instead causes PD fluid pump 24 to pump air initially to place negative pressure on flexible diaphragms 44 to pull fresh PD fluid from PD fluid container 106*a*, for example, through valves 28*g* and 28*i*, and into the fresh PD fluid sides of volumetric balancing chambers 40*a* and 40*b*, respectively. Control unit 50 then causes PD fluid pump 24 to pump air in the opposite direction to place positive air pressure on the flexible diaphragms 44 of volumetric balancing chambers 40*a* and 40*b* to discharge fresh PD fluid therefrom. The fresh PD fluid travels through valves 28*g* and 28*i* and valves 28*f* and 28*e* into output lumen 108*a* and patient line 108. The above process (drawing fresh PD fluid into volumetric balancing chambers 40*a* and 40*b* and discharging same from the balancing chambers by pumping air at PD fluid pump 24) is repeated until enough fresh PD fluid resides within patient line 108 to fill the used PD fluid or effluent side of volumetric balancing chambers 40*a* and 40*b*, or at least enough of same so that PD fluid pump 24 can pump fresh PD fluid back and forth between the volumetric balancing chambers.

Control unit 50 then performs the initial patient fill using the above process (drawing fresh PD fluid into volumetric balancing chambers 40*a* and 40*b* and discharging same from the balancing chambers) but does so now by pumping fresh PD fluid back and forth between the effluent sides of volumetric balancing chambers 40*a* and 40*b* instead of air. Control unit 50 performs the initial patient fill (and all subsequent patient fills according to above fill and discharge) by metering fresh, heated (at heater 26*a* under control of control unit 50) PD fluid to the patient via patient line 108 until a prescribed amount of fresh PD fluid is delivered. It should be appreciated that subsequent patient fills (any after the initial patient fill) occur after a patient drain in which the used PD fluid or effluent side of volumetric balancing chambers 40*a* and 40*b* is primed with used PD fluid or patient effluent from the prior drain.

In an alternative embodiment, control unit 50 causes system 10*a* to be primed fully (including fresh and used PD fluid sides of volumetric balancing chambers 40*a* and 40*b*) prior to the patient connecting to PD machine 20*a*. Here, fresh PD fluid is pumped through both sides of volumetric balancing chambers 40*a* and 40*b* and eventually to drain via drain line 112.

For patient filling in any of the systems and PD cyclers discussed herein, volumetric accuracy may be monitored and controlled in one or more way. One way is discussed above for patient draining, which is for control unit 50 to count accurate pump fill strokes made by PD fluid pump 24. That is, the amount of fluid pumped back and forth between volumetric balancing chambers 40*a* and 40*b* via three-way valves 28*n* and 28*o* should equal the amount of fresh, heated PD fluid discharged from volumetric balancing chambers 40*a* and 40*b* to the patient. The other way is for control unit 50 to count and accumulate the number of discharge strokes made by each of volumetric balancing chambers 40*a* and 40*b*. The volumes of the fixed volume chambers 42 of volumetric balancing chambers 40*a* and 40*b* are known so that each time fresh PD fluid is discharged from the chambers, the incremental volume may be accumulated by control unit 50. Pressure sensors 34*a* and 34*b* operating with volumetric balancing chambers 40*a* and 40*b*, respectively, are well-positioned to detect when flexible diaphragms 44 dead end against a wall of fixed volume chambers 42, confirming that a full stroke of fresh PD fluid has been discharged from the fixed volume chambers. Control unit 50 may employ both methods for monitoring filling accuracy for comparison and/or for calibrating PD fluid pump 24 for the next patient drain where the accuracy of PD fluid pump 24 is needed.

Referring now to FIG. 2, an example "germ deactivation" (sterilization/disinfection) sequence for PD machine 20*a* of system 10*a* is illustrated. The teachings of the "germ deactivation" sequence are applicable to any of the PD machines and associated systems discussed herein. Here, at the end of treatment, the patient or caregiver removes PD fluid containers 106*a* to 106*c*. Spring-loaded doors 30*a* to 30*c* automatically close over reusable solution lines 102*a* to 102*c*, respectively, which are sealingly plugged into sterilization ports 32*a* to 32*c*. A sterilization loop is thereby formed, which includes reusable solution lines 102*a* to 102*c*, the reusable lines within PD machine 20*a* that lead to the fresh PD fluid sides of volumetric balancing chambers 40*a* and 40*b*, the fresh PD fluid sides themselves and output port 46*a*.

At the end of treatment, the patient or caregiver also removes patient line 108 (including output lumen 108*a* and return lumen 108*b*) and drain line 112 from ports 46*a* to 46*c*, respectively. Sealed cover 48 covers, e.g., spring-closes over exposed output port 46*a* to seal the port and force sterilization fluid back into the sterilization loop. Sealed covers 48 also, e.g., spring-close over exposed ports 46*b* to 46*c* to seal the ports and force disinfection fluid back into a disinfection loop that also includes the used PD fluid or effluent side of PD machine 20*a* up to and including the used sides of volumetric balancing chambers 40*a* and 40*b*. The disinfection loop at the end of treatment is full of used PD fluid or patient effluent, which may be used for the disinfection sequence if desired. If fresh PD fluid is desired for disinfection instead, then control unit 50 causes PD fluid pump 24 to pump a disinfection loop volume's worth of fresh PD fluid into patient line 108 prior to its removal. Control unit 50 also causes PD fluid pump 24 to pull the fresh PD fluid into the disinfection loop from patient line 108 and push the used PD fluid from the disinfection loop to a drain container or house drain via drain line 112 prior to its removal. The disinfection loop or used PD fluid side of volumetric balancing chambers 40*a* and 40*b* is now primed with leftover fresh PD fluid for disinfection. The sterilization loop or fresh PD fluid side of volumetric balancing chambers 40*a* and 40*b* is also now primed with leftover fresh PD fluid for sterilization.

In an embodiment, it does not matter which "germ deactivation" portion takes place first, sterilization or disinfection. The two sequences may overlap, however the sterilization sequence needs to sterilize the fresh PD fluid sides of volumetric balancing chambers 40*a* and 40*b*, while the disinfection sequence needs to disinfect the used PD fluid sides of the volumetric balancing chambers. It may not be possible to sterilize and disinfect volumetric balancing chambers 40*a* and 40*b* at the same time. Moreover, PD fluid pump 24 is needed in both sterilization and disinfection sequences and may not be able to perform double duties simultaneously.

For sterilization, it is contemplated that control unit 50 receives feedback from temperature sensor 36*a* to cause sterilization/treatment heater 26*a* to heat the leftover fresh PD fluid in the sterilization loop to a desired sterilization temperature of, for example, 120° C. or higher. PD fluid pump 24 pumps leftover PD fluid back and forth between the used PD fluid sides of volumetric balancing chambers 40*a* and 40*b*, causing heated leftover PD fluid in the sterilization loop to be circulated back and forth to contact and sterilize all areas of the sterilization loop. The areas of the sterilization loop contacted with superheated PD fluid include reusable solution lines 102*a* to 102*c*, sterilization ports 32*a* to 32*c*, valves 28*a* to 28*i*, associated lines, the fresh PD fluid sides of volumetric balancing chambers 40*a* and 40*b*, and output port 46*a*. Any one or more or all of valves 28*a* to 28*i* may be toggled open and closed during the sterilization sequence to aid the sterilization. Control unit 50 concludes the sterilization sequence after a sufficient FO sterilization dose is delivered to the sterilization loop, e.g., after fifteen to twenty minutes of sterilization recirculation at 120° C. or higher.

For disinfection, which may again occur before or after or overlap with the sterilization sequence, it is contemplated that control unit 50 receiving feedback from temperature sensor 36*b* cause disinfection heater 26*b* to heat the disinfection loop fluid (e.g., leftover fresh or used PD fluid) to a desired sterilization temperature of, for example, 65° C. or 75° C. or higher.

PD fluid pump 24 pumps disinfection loop fluid (e.g., leftover fresh or used PD fluid) back and forth between the used PD fluid sides of volumetric balancing chambers 40*a* and 40*b*, and throughout the disinfection loop, causing heated disinfection loop fluid (e.g., leftover fresh or used PD fluid) in the disinfection loop to be circulated back and forth to contact and disinfect all areas of the disinfection loop. The areas of the disinfection loop contacted with heated disinfection loop fluid (e.g., leftover fresh or used PD fluid) include valves 28*j* to 28*o* and associated lines, the used PD fluid sides of volumetric balancing chambers 40*a* and 40*b*, and ports 46*b* and 46*c*. Any one or more or all of valves 28*j* to 28*o* may be toggled open and closed (two-way) or toggled between positions or orientations (three-way) during the disinfection sequence to aid the disinfection. Control unit 50 concludes the disinfection sequence after a sufficient A0 disinfection dose is delivered to the disinfection loop, e.g., after forty-five minutes at 75° C. or higher, assuming a disinfection loop volume of around 100 to 150 milliliters. Larger or smaller disinfection loop volumes would require longer and shorter disinfection times, which is due primarily to longer or shorter warmup times associated with larger or smaller disinfection loop volumes.

Figure 3:
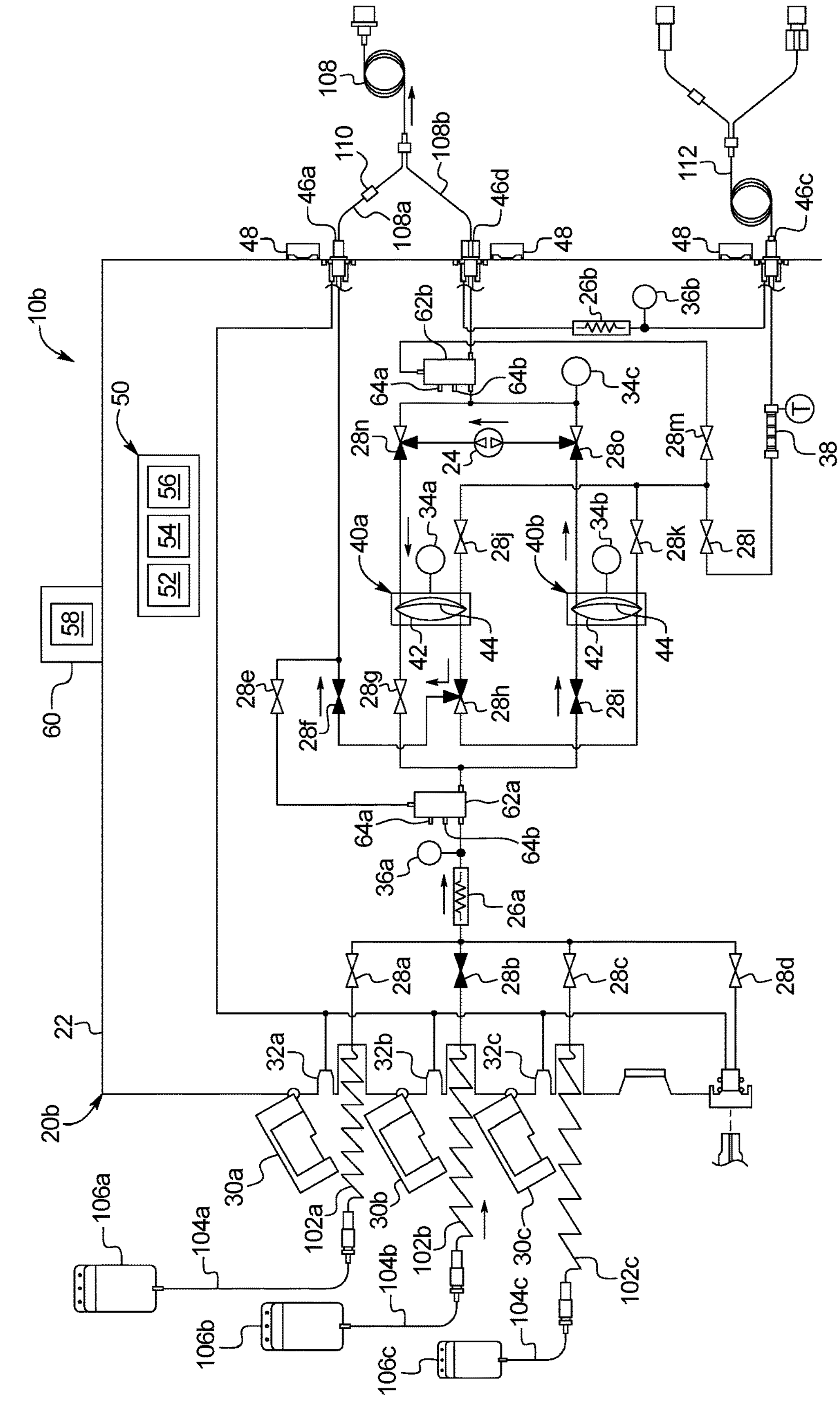
FIG. 3 is a schematic view of another embodiment of a peritoneal dialysis ("PD") machine and associated system having a single pump located on a used PD fluid side of the machine.

Referring now to FIG. 3, PD fluid machine 20*b* of system 10*b* illustrates an alternative embodiment of the present disclosure. PD fluid machine 20*b* of system 10*b* includes each of the features, structure and alternatives described above for PD fluid machine 20*a* of system 10*a*. All such structure, functionality and alternatives are incorporated by reference into PD fluid machine 20*b* of system 10*b*.

In PD fluid machine 20*a* of system 10*a*, air in the fresh and used PD fluid sides of the system tends to collect in volumetric balancing chambers 40*a* and 40*b*. The air may be detected using pressure sensors 34*a* and 34*b*. Once the amount of air in volumetric balancing chambers 40*a* and 40*b* reaches a threshold, control unit 50 causes the air to be purged to a drain container or house drain via drain line 112 (air on the fresh PD side may be pushed into the used PD fluid side via return lumen 108*b* of patient line 108 and from there to drain).

To prevent or mitigate air entering volumetric balancing chambers 40*a* and 40*b*, PD fluid machine 20*b* of system 10*b* provides a fresh PD fluid airtrap 62*a* on the fresh PD fluid side of machine 20*b* and a used PD fluid airtrap 62*b* on the used PD fluid side of machine 20*b*. Each of airtraps 62*a* and 62*b* operates with one or more level sensor 64*a* and 64*b* that output to control unit 50. One or more level sensor 64*a*, 64*b* ensure(s) that a desired level or range of levels of fresh and used PD fluid are maintained in the respective airtrap. Level sensors 64*a*, 64*b* may be ultrasonic sensors or any other type of sensor that can detect between PD fluid and air.

Airtraps 62*a* and 62*b* allow more air to be tolerated in system 10*b*. More air may be collected before control unit 50 needs to perform an air purge routine. Also, when an air purge routine is needed, air may be purged from airtraps 62*a* and 62*b* during a dwell phase of the treatment. Airtraps 62*a* and 62*b* are sized in an embodiment to hold a full volume's worth of air generated in each patient fill (airtrap 62*a*) and each patient drain (airtrap 62*b*) so that the purging of air may occur during a patient dwell. It is a goal of system 10*b* to attempt to trap air in airtraps 62*a* and 62*b* prior to the air reaching balancing chambers 40*a* and 40*b*, which could affect their volumetric accuracy.

Figure 4:
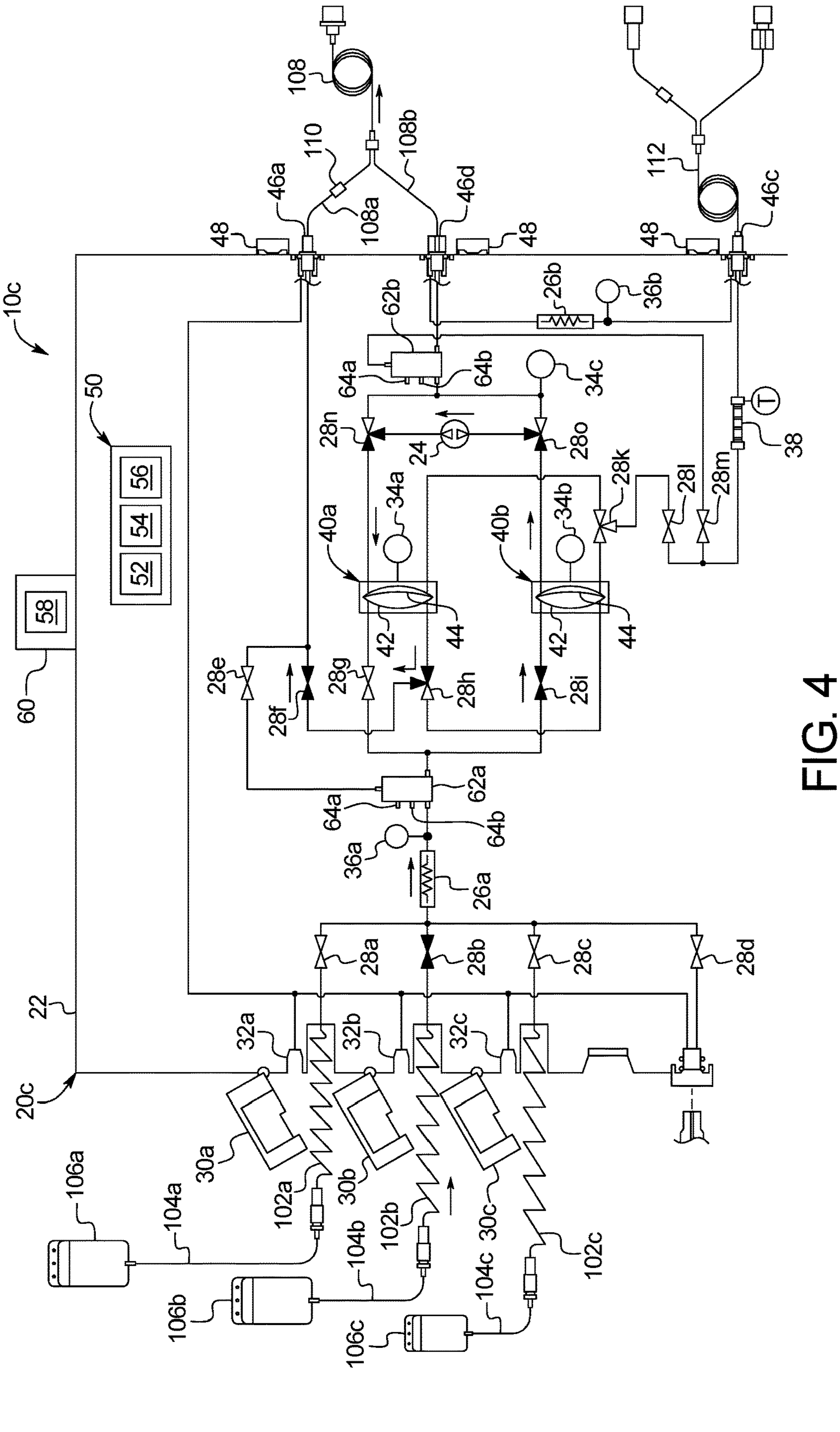
FIG. 4 is a schematic view of a third embodiment of a peritoneal dialysis ("PD") machine and associated system having a single pump located on a used PD fluid side of the machine.

Referring now to FIG. 4, PD fluid machine 20*c* of system 10*c* illustrates another alternative embodiment of the present disclosure. PD fluid machine 20*c* of system 10*c* includes each of the features, structure and alternatives described above for PD fluid machines 20*a* and 20*b* of systems 10*a* and 10*b*. All such structure, functionality and alternatives are incorporated herein by reference into PD fluid machine 20*c* of system 10*c*. PD fluid machine 20*c* of system 10*c* includes airtraps 62*a* and 62*b* as discussed above for PD fluid machine 20*b* of system 10*b*. PD fluid machine 20*c* of system 10*c* removes two-way valve 28*j* in PD fluid machine 20*b* of FIG. 3. Also, two-way valve 28*k* in PD fluid machine 20*b* of FIG. 3 is a three-way valve in PD fluid machine 20*c* of FIG. 4. PD fluid machine 20*c* of FIG. 4 accordingly includes one less valve than PD fluid machine 20*b* of FIG. 3. It should be appreciated that those of skill in the art may be able to determine many different ways to valve PD systems of the present disclosure. PD fluid machine 20c of system 10c provides one example.

Figure 5:
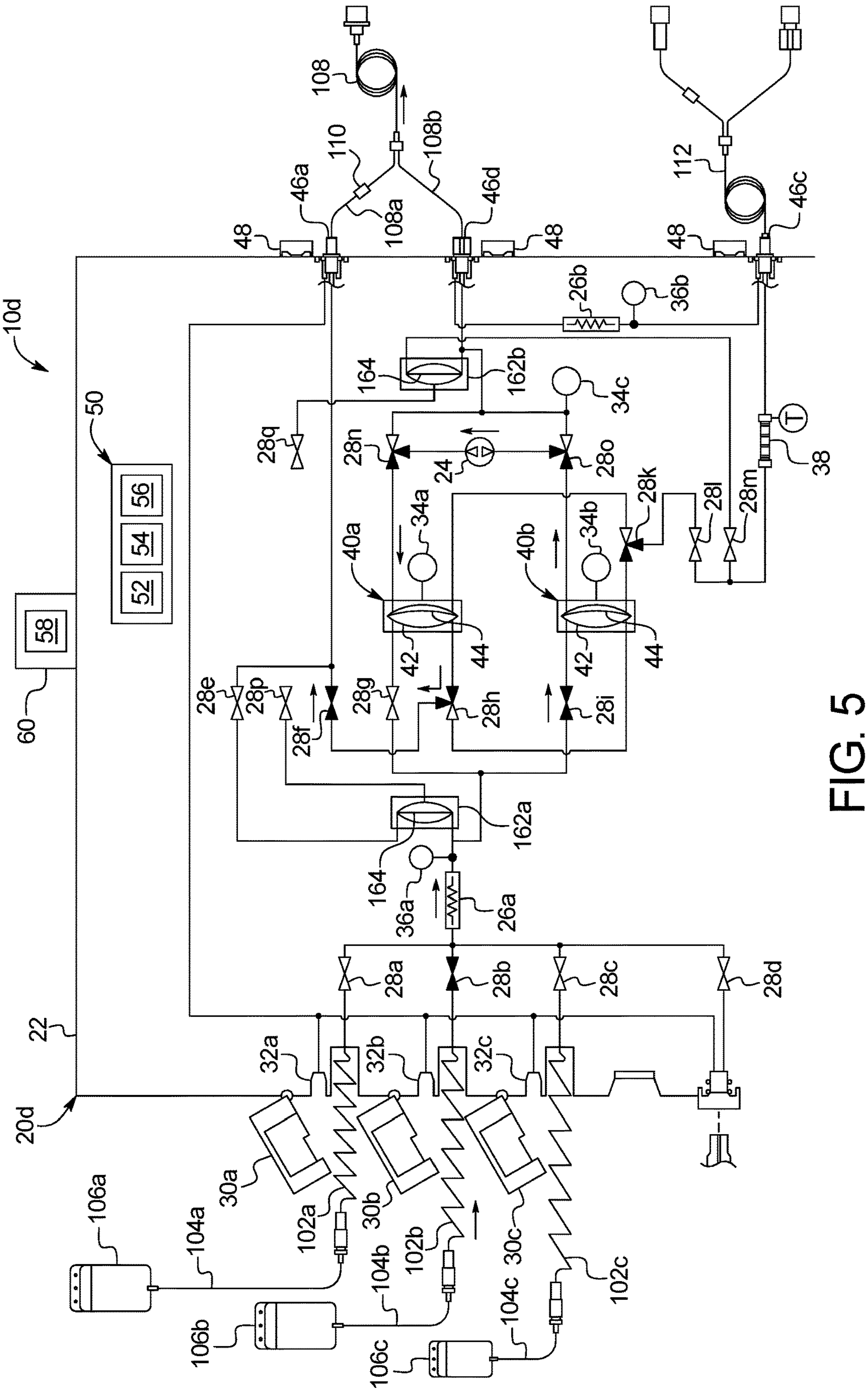
FIG. 5 is a schematic view of a third embodiment of a peritoneal dialysis ("PD") machine and associated system having a single pump located on a used PD fluid side of the machine.

Referring now to FIG. 5, PD fluid machine 20d of system 10d illustrates yet another alternative embodiment of the present disclosure. PD fluid machine 20d of system 10d includes each of the features, structure and alternatives described above for PD fluid machines 20a to 20c of systems 10a to 10c, respectively. All such structure, functionality and alternatives are incorporated herein by reference into PD fluid machine 20d of system 10d. The primary difference with PD fluid machine 20d of system 10d is the provision of alternative airtraps 162a and 162b in the fresh PD fluid side and the used PD fluid side of PD machine 20d, respectively.

One issue with airtraps 62a and 62b of PD machines 20b and 20c is that they are stiff and may leak or squirt fresh or used PD fluid if a pressure exists above ambient in the surrounding fluid lines and a door of PD fluid machine 20d is opened. Such pressure building may occur after a disinfection/sterilization phase, for example, before the fluid temperature has a chance to cool. Present alternative airtraps 162a and 162b mitigate the pressure-building issue by providing flexible membranes 164. At the start of the "germs deactivation" (sterilization/disinfection) sequence, control unit 50 positions membranes 164 within airtraps 162a and 162b such that there a sufficient amount of air residing on the non-fluid contacting sides of membranes 164. When the "germs deactivation" sequence has been completed, the air on the non-fluid contacting sides of the back sides of the membranes 164 is released via control unit 50, e.g., through vent valve 28p for airtrap 162a and through vent valve 28q for airtrap 162b. The release of air from airtraps 162a and 162b relives pressure in the fresh and used PD fluid sides of PD machine 20c, respectively, without allowing air into system 10d that could destroy the germ-free status of the fresh and used sides after sterilization/disinfection.

It should be understood that various changes and modifications to the presently preferred embodiments described herein will be apparent to those skilled in the art. For example, while heat is disclosed as the mechanism for sterilization and disinfection, it should be appreciated that other types of disinfection are possible alternatively or additionally, such as, chemical disinfection and/or UV radiation. It is therefore intended that such changes and modifications be covered by the appended claims.

The invention claimed is:

1. A peritoneal dialysis ("PD") system comprising:

a first volumetric balancing chamber including a first fixed volume chamber and a first diaphragm positioned and arranged to extend back and forth within the first fixed volume chamber, the first diaphragm separating a fresh PD fluid side from a used PD fluid side of the first volumetric balancing chamber;

a second volumetric balancing chamber including a second fixed volume chamber and a second diaphragm positioned and arranged to extend back and forth within the second fixed volume chamber, the second diaphragm separating a fresh PD fluid side from a used PD fluid side of the second volumetric balancing chamber; and a PD fluid pump positioned and arranged to pump used PD fluid back and forth between the used PD fluid sides of the first and second volumetric balancing chambers.

2. The PD system of claim 1, which includes at least one valve in fluid communication with the fresh PD fluid side of one of the first or second volumetric balancing chambers, and wherein fresh PD fluid is discharged from the fresh PD fluid side through the at least one valve when the PD fluid pump pumps used PD fluid to the used PD fluid side of the first or second volumetric balancing chamber.

3. The PD system of claim 2, which includes a control unit configured to operate the PD fluid pump, the control unit configured to determine an amount of fresh PD fluid discharged from the fresh PD fluid side of the first or second volumetric balancing chamber via (i) monitoring a pumping output of the PD fluid pump and/or (ii) using a known volume of the first or second fixed volume chamber.

4. The PD system of claim 1, which includes at least one valve in fluid communication with the fresh PD fluid side of the first or second volumetric balancing chamber, and wherein fresh PD fluid is drawn into the fresh PD fluid side through the at least one valve when the PD fluid pump pumps used PD fluid from the used PD fluid side of the first or second volumetric balancing chamber.

5. The PD system of claim 1, which is configured during a patient drain such that the PD fluid pump pumps used PD fluid through a patient line, through one of the first or second volumetric balancing chambers, and through a drain line.

6. The PD system of claim 5, wherein the PD fluid pump pumps used PD fluid through a return lumen of the patient line, and wherein the patient line further includes an output lumen for delivering fresh PD fluid to a patient.

7. The PD system of claim 5, which includes a control unit configured to operate the PD fluid pump during the patient drain, the control unit configured to determine an amount of used PD fluid removed during the patient drain via monitoring at least one pumping output of the PD fluid pump.

8. The PD system of claim 1, which includes a first heater in fluid communication with the fresh PD fluid sides of the first and second volumetric balancing chambers, and a second heater in fluid communication with the used PD fluid sides of the first and second volumetric balancing chambers, wherein the first heater is used in a sterilization sequence and the second heater is used in a disinfection sequence.

9. The PD system of claim 8, wherein the first heater is further used to heat fresh PD fluid for treatment.

10. The PD system of claim 8, wherein the first heater heats fresh PD fluid to at least 120° C. for the sterilization sequence, and the second heater heats fresh or used PD fluid to at least 65° C. for the disinfection sequence.

11. The PD system of claim 1, which includes a sterilization loop including the fresh PD fluid sides of the first and second volumetric balancing chambers and at least one of (i) at least one reusable solution line or (ii) at least one sealed cover that closes over at least one patient line port and/or drain line port.

12. The PD system of claim 1, which includes a disinfection loop including the used PD fluid sides of the first and second volumetric balancing chambers and at least one sealed cover that closes over at least one patient line port and/or drain line port.

13. The PD system of claim 1, which is configured to run a patient drain in which (i) the first and second volumetric balancing chambers are bypassed and the accuracy of PD fluid pump is relied upon or (ii) the first and second volumetric balancing chambers are operated.

* * * * *